United States Patent [19]

Dwyer et al.

[11] 4,258,218

[45] Mar. 24, 1981

[54] CONVERSION OF ALCOHOLS OR ETHERS USING RARE EARTH ALUMINA

[75] Inventors: Francis G. Dwyer, West Chester; Albert B. Schwartz, Philadelphia, both of Pa.

[73] Assignee: Mobil Oil Corporation, New York, N.Y.

[21] Appl. No.: 6,408

[22] Filed: Jan. 25, 1979

Related U.S. Application Data

[62] Division of Ser. No. 861,767, Dec. 19, 1977, Pat. No. 4,156,698, which is a division of Ser. No. 794,163, May 5, 1977, abandoned.

[51] Int. Cl.$^3$ ............................................ C07C 41/09
[52] U.S. Cl. .................................... 568/698; 252/462
[58] Field of Search ...................... 568/698; 252/462

[56] References Cited

U.S. PATENT DOCUMENTS

| | | | |
|---|---|---|---|
| 2,014,408 | 9/1935 | Woodhouse | 568/698 |
| 3,714,071 | 1/1973 | Michalko | 252/462X |
| 3,741,725 | 6/1973 | Graham | 252/466 X |
| 3,928,483 | 12/1975 | Chang et al. | 568/698 |
| 4,035,430 | 7/1977 | Dwyer et al. | 568/698 |
| 4,056,489 | 11/1977 | Hindin et al. | 252/462 |
| 4,058,576 | 11/1977 | Chang et al. | 568/698 |
| 4,061,594 | 12/1977 | Michel et al. | 252/462 |

*Primary Examiner*—Howard T. Mars
*Attorney, Agent, or Firm*—Charles A. Huggett; Michael G. Gilman; Claude E. Setliff

[57] ABSTRACT

An improved process using a rare earth-containing catalyst is provided. The catalyst comprises a composite of matrix and rare earth or of zeolite, rare earth and matrix, usually alumina. The rare earth can be a single metal or a mixture of rare earth metals. The process involved is the conversion of alcohols or ethers to gasoline boiling range hydrocarbons.

5 Claims, No Drawings

CONVERSION OF ALCOHOLS OR ETHERS USING RARE EARTH ALUMINA

CROSS REFERENCE TO RELATED APPLICATIONS

This application is a division of copending Application Ser. No. 861,767, filed Dec. 19, 1977, now U.S. Pat. No. 4,156,698 which in turn is a division of Application Ser. No. 794,163, filed May 5, 1977, now abandoned.

BACKGROUND OF THE INVENTION

1. Field of the Invention

The invention relates to a process of converting alcohols or ethers to gasoline fractions by passing them over a catalyst comprising a composite or a zeolite, and/or a matrix material and a rare earth metal or mixtures of such metals.

2. Description of the Prior Art

A continuing growth in the production of synthetic fibers, plastic and rubber has taken place in recent decades. This growth, to a very large extent, has been supported and encouraged by an expanding supply of petrochemical raw materials such as ethylene, benzene, toluene, and xylenes. Side by side with this development, there has been an increasing demand for aromatic hydrocarbons for use as high octane gasoline components. Environmental factors which limit the lead content of gasoline are likely to aggravate the need for aromatics.

Burgeoning demand for olefins, particularly ethylene, and for aromatic hydrocarbons, has of course led to periods of shortage, either due to short supply of suitable feedstocks or to limited processing capacity. In any case, it would appear desirable to provide efficient means for converting raw materials other than petroleum to olefins and aromatic hydrocarbons.

The process described herein employs zeolites that are known in the art. ZSM-5, for example, is disclosed and claimed in U.S. Pat. No. 3,702,886. A description of ZSM-11 may be found in U.S. Pat. No. 3,709,979 and ZSM-12 in West German Offenlaugunschrifft 2,213,109. The patents referred to are incorporated herein by reference.

ZSM-4 is described in U.S. Pat. No. 3,923,639, and the descriptive matter of this patent relating to such zeolite is hereby incorporated by reference in this application.

ZSM-35 is disclosed in U.S. application No. 528,061, filed Nov. 29, 1974. Descriptions of ZSM-38 and ZK-4 can be found in U.S. application No. 560,412, filed Mar. 20, 1975 and U.S. Pat. No. 3,140,252, respectively. So these zeolites may be completely described, these applications and the patent are incorporated herein by reference.

U.S. Pat. No. 3,816,342 claims a process involving exchanging a zeolite, calcining it, compositing it with a matrix and exchanging it again. The catalyst is disclosed as being useful in hydrocarbon conversion reactions.

SUMMARY OF THE INVENTION

In accordance with the present invention, there are provided a process for converting a feed comprising a $C_1$–$C_4$ monohydric alcohol to its ether using a rare earth alumina catalyst and a process for converting said alcohol, its ether derivative or mixtures thereof to a gasoline boiling range hydrocarbon or to a light olefin such as $C_2=$ by contacting the latter feed with a composite comprising a zeolite, a matrix therefor and a rare earth metal or mixture of rare earth metals. The catalyst per se is also provided by the invention.

DESCRIPTION OF SPECIFIC EMBODIMENTS

Any composition consisting essentially of one or more monohydric alcohols having from 1 to 4 carbon atoms, mixtures thereof and mixtures with the compounding ethers, may be used as feed to the process of this invention. Thus, methanol, ethanol, n-propanol, isopropanol, n-butanol, sec-butanol and isobutanol may be used either alone or in admixture with one another. The ethers useful in the invention include, alone, or in admixtures, dimethyl, diethyl, dipropyl and dibutyl ethers, as well as methylethyl ether and the like. Particularly preferred feeds are methanol, dimethyl ether and mixtures thereof.

The zeolites that may be used include the natural zeolites such as mordenite, erionite, chabazite, clinoptilolite, offretite, mazzite and the like as well as the synthetic zeolites Alpha, Beta, ZSM-4, ZSM-5, ZSM-11, ZSM-12, ZSM-35 and ZSM-38.

The alumina matrix or carrier useful in the invention may be any alumina that has a high surface area (i.e. $>50 m^2/g$) and exhibits good binding properties. Aluminas meeting these criteria are the gamma, eta, chi, rho, or kappa forms thereof. There matrix materials may be formed using the appropriate hydrated alumina forms, such as the pseudoamorphous trihydrate, $\beta$-trihydrate, $\alpha$-monohydrate, pseudobohemite, $\gamma$-trihydrate and $\alpha$-trihydrate and calcining the product.

Rare earth elements that may be used alone or in combination include lanthanum, cerium, praseodymium, neodymium, promethium, samarium, europium, gadolinium, terbium, dysprosium, holmium, erbium, thulium, ytterbium, ytterium and lutetium. The rare earth element, expressed in terms of its oxide, $RE_2O_3$, is employed within the range of from about 1% to about 30% by weight of the matrix, preferably from about 2% to about 20%. This means that, of the $RE_2O_3.Al_2O_3$ portion, the $Al_2O_3$ content will range from about 99% to about 70% by weight of the total.

With respect to the composite, it will comprise from about 5% to about 80% by weight thereof of the zeolite, preferably from about 20% to about 75%, and from about 95% to about 20% by weight of $RE_2O_3.Al_2O_3$, preferably from about 80% to about 25%.

The rare earth elements may be incorporated with the alumina as salts or hydrated oxides. The alumina itself may be impregnated with the RE salts, as, for example, nitrate or halide. The $RE_2O_3.Al_2O_3$ portion is then mixed with the zeolite in anyway suitable, the composite is formed into suitable sizes and shapes and is calcined at a temperature of from about 800° F. to about 1700° F. For maximum inertness of the matrix, the calcination is carried out within the range of from about 1200° F. to about 1700° F., but below the temperature at which substantial zeolite destruction occurs.

In preparing the composite, the zeolite and alumina (which may contain about 1–10% by weight of $SiO_2$ as a stabilizing agent) may be mixed before the rare earth element is added. In this case, the rare earth can be added by impregnation and then treated as outlined already.

The zeolites, whether per se or in the composite, or whether having rare earth elements incorporated therewith or not, are capable of having at least a portion of the original cations associated therewith replaced by a wide variety of other cations according to techniques well known in the art. Replacing cations include ammonium and metal cations, including mixtures of the same. The zeolite employed as catalyst in this invention may be prepared from zeolites wherein at least a portion of the original cations associated therewith have been replaced by hydrogen.

The crystalline aluminosilicate zeolites can be converted to the hydrogen form, i.e., having at least a portion of the original cations associated therewith replaced by hydrogen, generally by two methods. The first involves direct ion exchange employing an acid. Suitable acids include both inorganic acids and organic acids. Typical inorganic acids which can be employed include hydrochloric acid, hydrosulfuric acid, nitric acid, nitrous acid, hyponitrous acid, phosphoric acid, and carbonic acid. Typical organic acids which can be employed are the monocarboxylic and polycarboxylic acids which can be aliphatic, aromatic, or cycloaliphatic in nature. Representative suitable acids include acetic, trichloroacetic, bromoacetic, citric, maleic, fumaric, itaconic, phenylacetic, benzene sulfonic and methane sulfonic acids. The second method for preparing the hydrogen form, which is preferred, involves first preparing an ammonium or other hydrogen ion precursor form by base exchange and then calcining to cause evolution of the ammonia leaving a hydrogen ion remaining on the zeolite. Calcining is carried out in air at 400° C.–600° C. for about 15 minutes to about 24 hours. Suitable compounds for preparing the hydrogen ion precursor form include ammonium compounds such as the chloride, bromide, iodide, bicarbonate, sulfate, citrate, borate, and palmitate. Still other ammonium compounds which can be employed include quaternary ammonium compounds such as tetramethylammonium hydroxide and trimethylammonium chloride.

In the process of this invention, the feed consisting essentially of one or more of the lower alcohols or ethers derived therefrom is contacted with the above-described catalyst at a temperature of about 250° C. to about 700° C., and preferably about 350° C. to 500° C.; a contact time equivalent to or the same as a weight hourly space velocity (WHSV) of about 0.5 to 50, preferably about 1.0 to 10.0, it being understood that WHSV signifies pounds of feed per pound of catalyst per hour; and at an absolute pressure of about 0.2 to 30 atmospheres. The catalyst may be in the form of fixed bed, fixed fluid bed, or it may be of the transport bed type.

The produce stream in the process of this invention contains steam and a hydrocarbon mixture comprising light olefins and aromatic hydrocarbons.

The predominant aromatic hydrocarbons are monocyclic hydrocarbons such as benzene, toluene and xylene. Thus, they are all valuable petrochemicals. The steam and hydrocarbons are separated from one another by methods well known in the art. The proportions may be varied by selecting reaction conditions within the purview specified above, olefins being favored by lower temperatures and in general by less severe conversion conditions.

Catalyst deactivated by coke deposited during the process may be reactivated by controlled regeneration using an oxygen containing regeneration medium and controlling the operating conditions to limit the maximum catalyst temperature to about 600° C. Such a regeneration can be completed in less than about 24 hours. Operation of the process of this invention in the presence of added hydrogen may sometimes retard aging.

It is not fully understood why the composite catalyst of this invention produces such desirable products. Nonetheless, the conversion of a single carbon feed, such as methanol, or its ether, with such high selectivity to monocyclic aromatics, is surprising.

Having described the invention in general terms, the following Examples are offered as illustrations. It is to be understood that they are merely illustrative and are not intended to limit the invention.

EXAMPLE 1

Alpha-alumina monohydrate was formed into extrudates, dried and calcined at 1400° F. in air. The calcined alumina extrudate was impregnated with an aqueous solution containing 17.3% of mixed rare earth chlorides to a level of 2.6 wt. % $RE_2O_3$, then recalcined at 1000° F. Rare earth solutions typically have the following composition:

Ce as $CeO_2 = 48\%$ by weight
La as $La_2O_3 = 24\%$ by weight
Pr as $Pr_6O_{11} = 5\%$ by weight
Nd as $Nd_2O_3 = 17\%$ by weight
Sm as $Sm_2O_3 = 3\%$ by weight
Gd as $Gd_2O_3 = 2\%$ by weight
Other rare earth oxides = 0.8% by weight To determine the effectiveness of the rare earth deactivation, the material was evaluated for the conversion of methanol to dimethyl ether at 850° F., since at this temperature alumina is a known catalyst for the decomposition of methanol into CO and $H_2$. The results are presented in Table 1 and are compared to those obtained with the same alumina starting material that had been calcined at 1200° F. without the addition of rare earth. These data show 15.1% by weight of CO in the product for the alumina alone while the rare earth-alumina gave only 1.5% by weight CO in the product.

TABLE 1

| | METHANOL DEHYDRATION | |
|---|---|---|
| | Catalyst Description | |
| | Kaiser $Al_2O_3$ calcined at 1200° F. | Kaiser $Al_2O_3$ calcined at 1400° F., impregnated with $RECl_3$ to 2.6% wt $RE_2O_3$ |
| Operating Conditions | | |
| Feed Comp. | 100% MeOH | 84% MeOH 16% $H_2O$ |
| Pressure, psig | 235 | 235 |
| WHSV, Hr | 9.8 | 9.5 |
| Temp., Avg. °F. | 852 | 854 |
| Temp., Max. °F. | 861 | 875 |
| MeOH Conv., % Wt. | 83.6 | 74.9 |

TABLE 1-continued

METHANOL DEHYDRATION

| | Catalyst Description | |
|---|---|---|
| | Kaiser Al$_2$O$_3$ calcined at 1200° F. | Kaiser Al$_2$O$_3$ calcined at 1400° F., impregnated with RECl$_3$ to 2.6% wt RE$_2$O$_3$ |
| Product Analysis, % by Weight | | |
| H$_2$O | 21.2 | 24.5 | 21.7[1] |
| MeOH | 16.6 | 21.5 | 25.7 |
| DME | 40.2 | 41.5 | 49.6 |
| CO | 15.1 | 1.5 | 1.8 |

[1] Calculated assuming 100% MeOH feed.

EXAMPLE 2

A catalyst comprising 65% ZSM-5 and 35% Al$_2$O$_3$ was processed into the catalytic acid form (i.e., exchange with the NH$_4^+$, followed by calcination). The catalyst was impregnated with an aqueous solution containing 4.2% by weight of mixed RE(NO$_3$)$_3$ to give a finished content of 1.1% RE$_2$O$_3$ on the overall catalyst. It was then dried and calcined at 1000° F. The catalyst was evaluated for the conversion of methanol to gasoline boiling range hydrocarbons. The results presented in Table 2 show the rare earth treated catalyst to give lower CO content, a methanol decomposition product, in the product at temperatures greater than 350° F. The data also indicate a higher aromatic content of the hydrocarbon product when using the rare earth treated catalyst. The rare earth in RE(NO$_3$)$_3$ was essentially the same as outlined in Example 1.

TABLE 2

METHANOL CONVERSION TO GASOLINE

| | Catalyst Description | |
|---|---|---|
| | 65% ZSM-5 35% Al$_2$O$_3$ | 65% ZSM-5, 35% Al$_2$O$_3$ Impregnated to 3.3% RE$_2$O$_3$ |
| Operating Conditions | | |
| Pressure, psig | 150 | 150 | 150 |
| WHSV, hr. | 5.7 | 5.7 | 5.7 |
| Temp., Max., °F. | 861 | 855 | 864 |
| Temp., Max., °F. | 883 | 878 | 895 |
| Product Analysis | | |
| C$_5$+, % by weight | 48.3 | 51.9 | 60.3 |
| Aromatics, % by weight | 18.4 | 23.2 | 25.4 |
| CO, % by weight | 1.1 | 0.8 | 0.6 |

We claim:

1. A process for converting a feed comprising a C$_1$–C$_4$ monohydric alcohol to its corresponding ether by contacting said feed with a catalyst comprising a composited rare earth and alumina.

2. The process of claim 1 wherein rare earth, expressed in terms of RE$_2$O$_3$, is present in an amount of from about 1% to about 30% by weight of said alumina.

3. The process of claim 1 wherein said alumina is alpha alumina.

4. The process of claim 1 wherein said rare earth is a mixture of rare earths.

5. The process of claim 1 wherein the feed is methanol.

* * * * *

UNITED STATES PATENT AND TRADEMARK OFFICE
CERTIFICATE OF CORRECTION

PATENT NO. : 4,258,218
DATED : March 24, 1981
INVENTOR(S) : Francis G. DWYER and Albert B. SCHWARTZ It is certified that error appears in the above-identified patent and that said Letters Patent are hereby corrected as shown below:

Column 2, line 41, "$RE_2O_3.Al2O_3$" should read --$RE_2O_3.Al_2O_3$--.

Column 6, line 23, "Temp.,Max.,°F" should read --Temp.,Avg.,°F--.

Column 6, line 39, "alpha" should read --gamma--.

Signed and Sealed this

Thirtieth Day of June 1981

[SEAL]

Attest:

RENE D. TEGTMEYER

Attesting Officer    Acting Commissioner of Patents and Trademarks